(12) United States Patent
Seccomandi et al.

(10) Patent No.: US 8,845,761 B1
(45) Date of Patent: Sep. 30, 2014

(54) FLUORESCENT WHITENING AGENT COMPOSITIONS

(71) Applicant: 3V Sigma S.p.A., Milan (IT)

(72) Inventors: Carlo Seccomandi, Bergamo (IT); Ivan Balestra, Bergamo (IT); Paolo Alioli, Bergamo (IT)

(73) Assignee: 3V Sigma S.P.A., Milan (IT)

( * ) Notice: Subject to any disclaimer, the term of this patent is extended or adjusted under 35 U.S.C. 154(b) by 0 days.

(21) Appl. No.: 13/834,509

(22) Filed: Mar. 15, 2013

(30) Foreign Application Priority Data

Mar. 15, 2013 (IT) .......................... MI2013A000365

(51) Int. Cl.
*D06L 3/00* (2006.01)
*D06L 3/02* (2006.01)

(52) U.S. Cl.
CPC ...................................... *D06L 3/025* (2013.01)
USPC ........................... 8/648; 8/654; 8/655; 8/688

(58) Field of Classification Search
USPC ...................................... 8/648, 654, 655, 688
See application file for complete search history.

(56) References Cited

U.S. PATENT DOCUMENTS

| 3,012,971 A | 12/1961 | Gessner et al. |
| 5,976,410 A | 11/1999 | Rohringer et al. |
| 2010/0159763 A1 | 6/2010 | Farrar et al. |

FOREIGN PATENT DOCUMENTS

| CN | 102093750 A | 6/2011 | |
| RU | 2223957 C2 | 2/2004 | |
| WO | 2005028749 A1 | 3/2005 | |
| WO | WO 2005/028749 A1 * | 3/2005 | ............. D21H 21/30 |

OTHER PUBLICATIONS

STIS Search Report dated May 2, 2014.*

* cited by examiner

*Primary Examiner* — Eisa Elhilo
(74) *Attorney, Agent, or Firm* — Silvia Salvadori, P.C.

(57) ABSTRACT

Disclosed are compositions containing:
 a) 25-60% by weight of compound of formula (1)

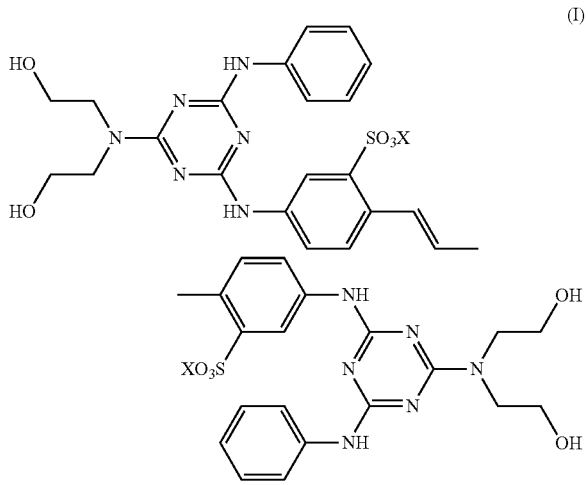

(I)

wherein X is hydrogen, an alkali or alkaline-earth metal, ammonium, alkylammonium and alkanolalkylammonium, alkanolammonium;
 b) at least 25% by weight of urea;
 c) up to 50% by weight of water.

12 Claims, No Drawings

FLUORESCENT WHITENING AGENT COMPOSITIONS

The present invention relates to fluorescent whitening compositions, processes for the preparation of said compositions, stable aqueous solutions of said compositions and the use of said compositions to bleach textile fibres and paper and in detergents.

PRIOR ART

The use of whitening agents to impart a higher degree of whiteness to products like paper, cardboard, fabrics and non-woven fabrics is well known. The whitening agents most commonly used in the paper and cardboard industry are derivatives of 4,4'-bis-[1,3,5-triazinyl]-diaminostilbene-2,2'-disulphonic acid substituted at the triazine ring with anilino and alkanolamino groups. The anilino groups can in turn contain other sulphonic groups, but as they increase the solubility in water of the corresponding molecules, they reduce the affinity of said molecules for the cellulose fibres constituting paper and fabric, leading to lower performance in terms of whiteness.

For reasons of ease of processing, the industry requires said whitening agents to be supplied in the fluid liquid forms of aqueous dispersion or, much more preferably, of solutions which are stable for at least a few months at temperatures ranging from 5 to 40° C.

As the stilbene whitening agents deriving from 4,4'-bis-[1,3,5-triazinyl]-diaminostilbene-2,2'-disulphonic acid substituted at the triazine ring with anilino groups and alkanolamino groups which are preferred by said industry are not readily water-soluble, the production of the corresponding concentrated, stable aqueous solutions formerly required the addition of significant amounts (up to 25% and over) of solubilising additives such as urea, caprolactam, ethylene glycol and polyglycols.

The solubilising additives just described certainly have the function of allowing the production of stable aqueous solutions of optical brighteners. However, their presence is undesirable, because when the brightener solution has been used, they are discharged into the waste water, and are consequently pollutants.

RU2223957 discloses a method for the preparation of derivatives of 4,4'-diaminostilbene-2,2' disulphonic acid in the form of aqueous solutions useful as optical brighteners. To obtain the solutions according to the invention, the method requires the conversion of the molecule of optical brightener to the corresponding acid form, its isolation, subsequent neutralisation with another base, and the addition of solubilising additives.

CS208507 discloses a stable liquid form of 4,4'-bis-(6-anilino-4-diethanolaminotriazin-2-ylamino)stilbene-2,2% disulphonic acid ammonium salt in dilute solution containing urea as solubilising additive. Once again, the process involves conversion of the optical brightener from the acid form.

CN102093750 discloses a method of preparing disulphonic optical brighteners in a stable liquid form wherein the optical brightener is dissolved in water in the simultaneous presence of numerous solubilising additives such as cellosolve, polyethylene glycol, polyols and urea. The potential pollutant content of these formulations is very high and undesirable.

U.S. Pat. No. 3,012,971 describes paper whitening compositions consisting of concentrated aqueous solutions of 4,4% bis-[2-phenylamino-4-diethanolamino-1,3,5-triazinyl]-diaminostilbene-2,2'-disulphonic acid or a salt thereof mixed with alkanolamines.

WO2005/028749 discloses aqueous compositions comprising stilbene whitening agents and alkanolamines.

U.S.2010/0159763 discloses aqueous compositions of fluorescent whitening agents, substituted at the triazine rings with propionamide amino groups, having the following formula:

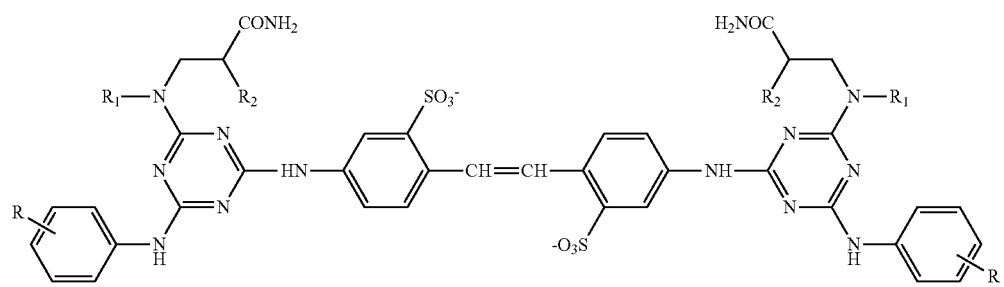

wherein at least 25% of the ions $[M^+]$ associated with the sulphonic group are substituted with $(CH_3)_2NH^+CH_2CH_2OH$ ions.

A further problem derives from the inevitable presence in the whitening agent solutions of inorganic chlorides such as sodium chloride, which derive from the whitening agent synthesis processes. In fact, all the industrial processes for the production of stilbene whitening agents substituted with triazine involve the use of cyanuryl chloride as reagent, whose reaction in successive steps with the various necessary amine products inevitably leads to the generation of large amounts of inorganic chlorides which are difficult to eliminate.

As the residual inorganic chlorides generate instability in the concentrated aqueous solutions of whitening agents, it has been essential to date to reduce their content significantly, inevitably using expensive osmotic separation techniques to obtain aqueous solutions which are stable over time.

Finally, U.S. Pat. No. 5,976,410 discloses aqueous dispersions, but not stable aqueous solutions, of optical brighteners: in column 1 from line 10 to line 23, to justify the production of concentrated dispersions, it is stated that stable aqueous solutions of optical brightener cannot be produced at concentrations exceeding 22% by weight because the content of solubilising agent must remain within an acceptable ratio compared with the content of brightener, and that after application, said solubilising agents, especially urea, are undesirable in the waste water resulting from the application process because they only act as pollutants.

All the compositions in stable solution described so far suffer from the drawback of being too dilute. For example, they do not exceed active ingredient contents of 25% by weight. Moreover, if any form of instability arises, said solutions produce sediments of packed product which are very difficult to recover, especially if the solution is in a container that cannot be stirred, like an ordinary tank. Finally, in view of the low concentration of optical brightener, their transport is uneconomical.

DESCRIPTION OF THE INVENTION

The purpose of the present invention is to provide a concentrated composition of whitening agents which is particularly stable in aqueous solution, even in the presence of the small amounts of inorganic chlorides that usually remain at the end of synthesis, is easy to produce, fluid and not excessively pollutant, or contains a proportion of solubilising additive lower than that of the optical brightener or comparable with that already used for the same systems as described, and more dilute.

It has now been found that in many cases, the concentrated compositions of the invention are even more environment-friendly than the corresponding more dilute stable compositions already known, as the proportion of solubilising agent required to stabilise a more concentrated solution of optical brightener according to the invention is significantly reduced.

It has also been found that the concentrated compositions of the invention are more resistant to low temperatures than the corresponding more dilute compositions.

In particular, unlike known compositions, which on cooling generate a precipitate that is not easily recoverable, the compositions of the invention remain in the form of clear viscous liquids or solidify into a vitreous, homogenous mass which easily returns to the liquid state and can therefore be completely regenerated simply by heating it to temperatures above 0 degrees centigrade.

The concentrated compositions of the invention are therefore particularly suitable for transport, even in environments with temperatures below 0° C., as they are stable or regeneratable, and easily diluted with water.

The optical brighteners used in the compositions of the invention are represented by compounds of formula (I):

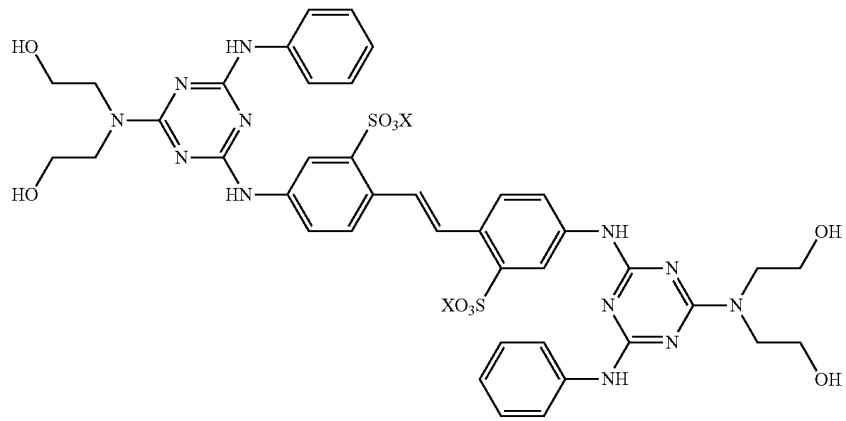

(I)

wherein X is hydrogen or an alkali or alkaline-earth metal, ammonium alkylammonium, alkanolalkylammonium or alkanolammonium.

X is preferably hydrogen, sodium, potassium, ammonium, ethanolamine, diethanolamine, triethanolamine or dimethylaminoethanol; more preferably, X is sodium.

The optical brighteners which can be used in the compositions of the invention are also hydrates of the compounds of formula (I).

The sodium salt of the compound of formula (I) is the most commercially widespread, and is identified by CAS number 4193-55-9.

The compositions of the invention comprise:
a) 25-60% by weight of compounds of formula (I);
b) min. 25% by weight of urea;
c) max. 50% by weight of water.

The compositions of the invention preferably comprise:
a) 30-50% by weight of compounds of formula (I);
b) min. 30% by weight of urea;
c) max. 40% by weight of water.

The compositions of the invention can easily be produced by simple mixing of the three ingredients added in any order at temperatures from 1° C. to 150° C., if necessary under pressure. It is preferable to operate under heating, generally from 50 to 100° C., at atmospheric pressure, and under stirring, to accelerate the dissolution of the optical brightener.

The process of synthesising optical brighteners is well known, and can be effected in a liquid system, consisting of one or more solvents, preferably selected from polar solvents such as ethers, ketones and mixtures thereof with water. Acetone, methyl ethyl ketone, acetone/water and methyl ethyl ketone/water can preferably be used. Even more preferably, mixtures of acetone and water wherein the acetone content ranges from 20% to 70% can be used.

The process generally comprises three reaction steps, wherein the cyanuryl chloride is reacted in succession, under different conditions and in the presence of bases, with three amino compounds, the most important of which is 4,4'-diaminostilbene-2,2'-disulphonic acid (DAS). The order of said three reactions can be changed, or one amino compound can be reacted first instead of another, and vice versa. In any event, at the end of the reactions, an organic phase is obtained consisting of optical brightener which can be separated from a salt-rich aqueous phase.

A very common process is the following:

At a first step of the process, cyanuryl chloride is reacted with 4,4'-diaminostilbene-2,2'-disulphonic acid (DAS) in a suitable solvent medium. Said reaction takes place at temperatures ranging from −20° C. to +20° C., and in the presence of bases such as sodium bicarbonate or sodium hydroxide, so that the pH of the system is from 1 to 7. The ratio of the moles of cyanuryl chloride to 4,4'-diaminostilbene-2,2'-disulphonic acid (DAS) at said step is about 2.00.

At a second step of the process, which usually takes place at temperatures ranging from +10° C. to +60° C., one mole of the product obtained from said first step is reacted with about 2 moles of aniline in the presence of bases such as sodium hydroxide, sodium bicarbonate or sodium carbonate, to maintain the reaction mixture at a pH preferably from 4 to 8. The suspension obtained in the first step is preferably used in the second step, without isolating the product.

At a third step of the process, the product obtained from said second step is reacted at a pH from 7 to 11 with at least 2 moles of alkanolamine, and preferably diethanolamine. Said third step preferably takes place at temperatures from 40° C. to 100° C. in the presence of bases such as sodium hydroxide, sodium carbonate or sodium bicarbonate, to maintain the pH from 7 to 11. At the end of the reaction the solvent is eliminated, for example by distillation, thus obtaining an aqueous suspension of the compound of formula (I), which separates. The organic liquid phase containing the product is separated under heating, for example from 80 to 100° C., from the lower aqueous phase consisting of a concentrated solution of salts.

At this point, the organic liquid phase, consisting of optical brightener and smaller amounts of saline solution, can preferably be directly formulated with urea and water to obtain the compositions according to the invention, with no need for particular operations to purify the optical brightener such as osmosis or precipitation of the acid form followed by re-neutralisation.

The compositions of the invention can also include further ingredients such as other whitening agents, inorganic salts, surfactants, preservatives, chelating agents, other solubilising agents or organic solvents.

Examples of optical whitening agents are optical tetra- and/or hexasulphonated stilbene brighteners.

Examples of inorganic salts are sodium sulphate, ammonium chloride and potassium chloride.

Examples of surfactants are sodium polynaphthalene sulphonates and ethoxylated fatty alcohols.

Examples of preservatives are glutaraldehyde, isothiazolinones and 2-bromo-2-nitropropane-1,3-diol.

Examples of usable chelating agents are EDTA and GLDA.

Examples of solubilising agents are polyethylene glycols and caprolactam.

Examples of organic solvents are ethylene and propylene glycols.

The compositions of the invention can be used to bleach natural, semisynthetic or synthetic fibres or paper, in the textile and detergent industries.

In particular, the solutions according to the invention can be used to bleach paper and cardboard at any point in the manufacturing process, either added directly to the fibre dispersion or in subsequent surface treatments such as coating and sizing.

The invention will be illustrated by reference to the following examples.

The concentrations of the optical whitening agent solutions are characterised by the $E^{1\%}_{1cm}$ parameter, which corresponds to the specific extinction value measured at the wavelength of maximum absorption of a solution containing 1% of the product in question, measured with an optical path of 1 cm.

In all examples, the extinction was measured with a Perkin-Elmer Lambda UV-VIS spectrophotometer with an optical path of 1 cm. The $E^{1\%}_{1cm}$ value of the compound with CAS number 4193-55-9 (purified powdered product, free of chlorides and moisture) is 568.

EXAMPLES OF FORMULATIONS (INVENTION)

Example 1

200 kg of end-of-reaction organic phase having a specific extinction of 350 and containing 61.6% by weight of optical brightener of formula (I), wherein X=Na, identified by CAS number 4193-55-9, was maintained at a temperature from 85° C. to 100° C., and then mixed with 123 kg of urea and 86 kg of water. The product was homogenised for about 15 minutes to obtain 409 kg of a stable, homogenous aqueous composition with the following characteristics:

$E^{1\%}_{1cm}$=171.15
Optical brightener CAS 4193-55-9=30.1% by weight
Urea=30.1%
Water=39.8%

Example 2

200 kg of end-of-reaction organic phase having a specific extinction of 346.5 and containing 61.0% by weight of optical brightener of formula (I), wherein X=Na, identified by CAS number 4193-55-9, was maintained at a temperature from 85° C. to 100° C., and then mixed with 92 kg of urea and 15 kg of water. The product was homogenised for about 15 minutes to obtain 307 kg of a stable, homogenous aqueous composition with the following characteristics:

$E^{1\%}_{1cm}$=225.5
Optical brightener CAS 4193-55-9=39.7% by weight
Urea=30.0%
Water=30.3%

Example 3

200 kg of end-of-reaction organic phase having a specific extinction of 350.0 and containing 61.6% by weight of optical brightener of formula (I), wherein X=Na, identified by CAS number 4193-55-9, was maintained at a temperature from 85° C. to 100° C., and then mixed with 86.07 kg of urea and 0.82 kg of water. The product was homogenised for about 15 minutes to obtain 286.89 kg of a stable, homogenous aqueous composition with the following characteristics:

$E^{1\%}_{1cm}$=244.0
Brookfield viscosity at 25° C.=1700 cps (RV3, 20 rpm)
Optical brightener CAS 4193-55-9=43.0% by weight
Urea=30.0%
Water 27.0%

Example 4

200 kg of end-of-reaction organic phase having a specific extinction of 350.0 and containing 61.6% by weight of optical brightener of formula (I), wherein X=Na, identified by CAS number 4193-55-9, was maintained at a temperature from 85° C. to 100° C., and then mixed with 66.5 kg of urea. The product was homogenised for about 15 minutes to obtain 266,5 kg of a stable, homogenous aqueous composition with the following characteristics:

$E^{1\%}_{1cm}$=262.7
Optical brightener CAS 4193-55-9=46.2% by weight
Urea=25.0% by weight
Water=28.8% by weight.

Example 5

40.0 kg of end-of-reaction organic phase having a specific extinction of 394.0 and containing 69.4% by weight of optical brightener of formula (I), wherein X=Na, identified by CAS no. 4193-55-9, was maintained at a temperature from 85° C. to 100° C., and then mixed with 25.78 kg of urea and 20.15 kg of water. The product was homogenised for about 15 minutes to obtain 85.93 kg of a stable, homogenous aqueous composition with the following characteristics:

$E^{1\%}_{1cm}$=183.4
Brookfield viscosity at 25° C.=90 cps (RV3, 100 rpm)
Optical brightener CAS 4193-55-9=32.3% by weight
Urea=30.0%
Water 37.7%.

Examples of Formulations (Comparison with Prior Art)

Example 6 (Comparison)

20 kg of end-of-reaction organic phase having a specific extinction of 366.7 and containing 64.6% by weight of optical brightener of formula (I), wherein X=Na, identified by CAS number 4193-55-9, was maintained at a temperature from 85° C. to 100° C., and then mixed with 6.0 kg of urea and 14.0 kg of water. The product was homogenised for about 15 minutes to obtain 40.0 kg of a homogenous aqueous composition with the following characteristics:

$E^{1\%}_{1cm}$=183.4
Optical brightener CAS 4193-55-9=32.3% by weight
Urea 15.0% by weight.
Water=52.7% by weight.

Example 7 (Comparison)

50 kg of end-of-reaction organic phase having a specific extinction of 343.5 and containing 60.5% by weight of optical brightener of formula wherein X=Na, identified by CAS number 4193-55-9, was maintained at a temperature from 95° C. to 100° C., and then mixed with 21.98 kg of urea and 65.42 kg of water. The product was homogenised for about 15 minutes to obtain 137.40 kg of a homogenous aqueous composition with the following characteristics:

$E^{1\%}_{1cm}$=125.0
Optical brightener CAS 4193-55-9=22.0% by weight
Urea=16.0% by weight
Water=62.0% by weight.

Example 8 (Comparison)

6.46 kg of water was eliminated by evaporation from 41.46 kg of end-of-reaction organic phase having a specific extinction of 394.0 and containing 69.4% by weight of optical brightener of formula (I), wherein X=Na, identified by CAS number 4193-55-9, to obtain 35.00 kg of oil with a specific extinction of 466.7, corresponding to 82.2% of active ingredient.

The sample was maintained at a temperature of about 95° C., 11.67 kg of urea was added, and the mixture was homogenised for about 15 minutes to obtain 46.67 kg of a composition with the following characteristics:

$E^{1\%}_{1cm}$=350.0
Optical brightener CAS 4193-55-9=61.6% by weight
Urea=25.0% by weight
Water 13.4% by weight.
Evaluation of Stability at 5° C.
All the samples 1 to 8 were subjected to T=5° C. for 40 days to assess their stability; surprisingly, samples 1, 2, 3, 4 and 5 remained clear and homogenous, and consequently stable, until the end of the test.

Samples 6, 7 and 8 (comparators) exhibited evident stability problems:
sample 6 formed a precipitate within 1 day, and therefore proved unstable.
sample 7 formed a precipitate within 10 days.
sample 8 completely solidified on simple cooling to below 50° C.

In all these cases it was impossible to regenerate and recover, by simple heating at room temperature, samples 6, 7 and 8 which had deteriorated following treatment at 5° C.
Evaluation of Stability at −15° C.
Samples 3, 4 and 5 were placed at an average temperature of −15° C. for 10 days.
Surprisingly, all the samples remained stable, in the form of clear, viscous liquids.
When heated to room temperature, all the samples returned to the fluid state and to the same viscosity values as recorded before the treatment.

Use—Application Example

The compositions of the invention can be used to bleach natural, semisynthetic or synthetic fibres or paper; the use of optical whitening agents considerably improves the optical properties of the paper treated, resulting in a high degree of whiteness. An application test in a mixture of virgin cellulose and precipitated calcium carbonate (PCC) is described below.

2.059 g of precipitated calcium carbonate (PCC) was added to 457.50 g of a mixture of short-fibre bleached eucalyptus cellulose with 38° SR (Schopper-Riegler) refinement and 3.00% dry matter, and divided into 5 parts.

The following amounts of a solution of sample 5 (optical brightener with specific extinction of 183.4) in demineralised water with a concentration of 2.00 g/l were added to the samples thus obtained, each of which contained 2.745 grams of dry cellulose:

0.00 (sample without optical whitening agent),
3.50 ml (equal to 0.26% of optical brightener in the dry paste)
7.00 ml (equal to 0.51% of optical brightener in the dry paste)
10.50 ml (equal to 0.77% of optical brightener in the dry paste)
14.00 ml (equal to 1.02% of optical brightener in the dry paste).

The samples thus obtained were homogenised under stirring for 15 minutes, and then used to form laboratory sheets with a Rapid-Koethen sheet former and dryer.

The degree of whiteness and colour coordinates of the samples thus obtained were recorded with an ELREPHO LWE450-X Datacolor reflectometer. The values obtained are set out in the table below:

| optical brightener | dose of optical brightener (% p) | D65/10° brightness | D65/10° CIE whiteness | L* | a* | b* |
|---|---|---|---|---|---|---|
| Sample 5 | 0.00 | 90.7 | 85.86 | 97.13 | 0.65 | 1.56 |
| | 0.26 | 102.9 | 121.73 | 97.82 | 2.81 | −6.20 |
| | 0.51 | 106.3 | 130.09 | 98.14 | 3.18 | −7.96 |
| | 0.77 | 107.9 | 133.52 | 98.28 | 3.28 | −8.68 |
| | 1.02 | 109.0 | 135.89 | 98.35 | 3.36 | −9.20 |

The invention claimed is:

1. Compositions comprising:
 a) 25-60% by weight of the compound of formula (I)

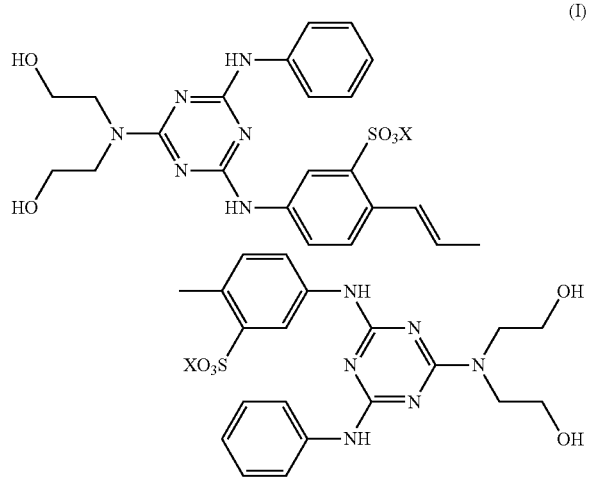

wherein X is hydrogen, an alkali or alkaline-earth metal, ammonium, alkylammonium and alkanolalkylammonium, alkanolammonium;
 b) at least 25% by weight of urea;
 c) up to 50% by weight of water.

2. Compositions according to claim 1 comprising:
 a) 30-50% by weight of compounds of formula (I);
 b) 30% by weight min. of urea;
 c) 40% by weight max. of water.

3. Compositions according to claim 1 wherein X is selected from hydrogen, sodium, potassium, ammonium, ethanolamine, diethanolamine, triethanolamine and dimethylaminoethanol.

4. Compositions according to claim 1 wherein X is sodium or potassium.

5. Compositions according to claim 1 also comprising other additives.

6. Compositions according to claim 5 wherein the additives are selected from whitening agents, inorganic salts, surfactants, preservatives, chelating agents, solubilisers or organic solvents.

7. Process for the preparation of the compositions of claim 1 which comprises mixing the three components in any order at temperatures ranging from 1° C. to 150° C., if necessary under pressure.

8. Process according to claim 7 which is carried out at a temperature from 50 to 100° C., under atmospheric pressure and under stirring.

9. Process according to claim 7 wherein the compound of formula (I) is prepared by subsequent reactions of cyanuryl chloride with three amino compounds to give an organic phase consisting of the compound of formula (I) which can be separated from a salt-rich aqueous phase.

10. Process according to claim 9 wherein the organic phase of the compound of formula (I) is directly formulated with urea and water without purification steps of the compound of formula (I).

11. A process for bleaching natural, semisynthetic or synthetic fibers or paper in the textile and detergent fields comprising applying to the natural, semisynthetic or synthetic fibers or paper a composition according to claim 1.

12. The process according to claim 11 bleaches paper and cardboard at any step of the preparation process, either directly by addition to the fibre dispersion, or by subsequent surface treatments with coating machines and size press coaters.

* * * * *